United States Patent [19]

Roth

[11] 4,241,186

[45] Dec. 23, 1980

[54] PECTIN CULTURE MEDIA AND METHOD

[75] Inventor: Jonathan N. Roth, Goshen, Ind.

[73] Assignee: Conviron, Inc., Goshen, Ind.

[21] Appl. No.: 970,347

[22] Filed: Dec. 18, 1978

[51] Int. Cl.$^3$ .............................................. C12N 1/00
[52] U.S. Cl. ................................... 435/243; 435/299; 435/810; 536/2
[58] Field of Search ................. 195/100, 99, 101, 102, 195/103, 127, 139; 536/2; 435/299, 240, 241, 245, 243, 810

[56] References Cited

U.S. PATENT DOCUMENTS

| | | | |
|---|---|---|---|
| 2,970,948 | 2/1961 | Stevens | 435/253 |
| 3,352,761 | 11/1967 | Moses | 195/100 X |
| 3,553,148 | 1/1971 | Bourland | 195/100 X |
| 3,622,559 | 11/1971 | Wiles | 536/2 |
| 3,741,877 | 6/1973 | Shaufus et al. | 195/127 |
| 3,814,670 | 6/1974 | Freake et al. | 195/127 |
| 3,935,067 | 1/1976 | Thayer | 195/100 X |
| 4,071,412 | 1/1978 | Eisenberg et al. | 195/100 X |

OTHER PUBLICATIONS

Levine, Compilation of Culture Media, Williams and Wilkins Publishers (1930) pp. 78–79 and 184.

*Primary Examiner*—R. B. Penland
*Attorney, Agent, or Firm*—Donald A. Kaul

[57] ABSTRACT

A method for preparing a gelled biological growth medium in a culture growth container which comprises combining a liquid growth medium including low methoxyl pectin and a multivalent metal cation material in the culture growth container. Preferably, the cation material is located on a support material, such as a filter pad or paper, and the liquid growth medium including the low methoxyl pectin material is poured over the support material while in the culture growth container.

7 Claims, No Drawings

PECTIN CULTURE MEDIA AND METHOD

BACKGROUND OF THE INVENTION

1. Field of the Invention

The present invention relates to the field of culture media and methods for producing the same, and more particularly to culture media including pectin as the gelling agent.

2. Description of the Prior Art

A considerable variety and number of culture media are disclosed in the prior art. A corresponding number of methods for producing such media are also known. In general, media used for the growth of living cells, tissues or organisms contain certain ingredients. These ingredients include water, nutrients (generally a carbon source, a nitrogen source, and smaller amounts of other essential elements), buffers, and often a gelling or solidifying agent.

The majority of the biological media present in the prior art utilize agar, gelatin or silica gel as solidifying agents, also referred to herein as gelling agents. Disadvantages are associated with each of these materials as solidifying agents. Agar is obtained from marine algae which must be harvested from naturally occurring populations. The supply of agar correspondingly fluctuates from year to year, while the demand for solidifying agent continues to grow. The price for agar has steadily increased as a result, and the present price is relatively high. Another problem associated with the use of agar is the need to dispense the agar into its container while quite warm, since the agar solution may solidify at about 40°–45° C. A temperature of 45° C. is too high for some cells to withstand without adverse effects.

Gelatin is easily obtained at a relatively reasonable cost, but it is easily hydrolyzed by many micro-organisms, which causes the gel to become a liquid. This is undesirable except in those cases where the hydrolysis is being used as a diagnostic biochemical test. Further, gelatin is generally available as a nutrient source for the organisms in contact with it, and as a result may interfere with the testing of specific nutrient sources. Gelatin also has the undesirable property of liquifying at quite low temperatures, so that media incorporating it as a gelling agent cannot be incubated above 25° C. with assurance that the medium will retain its solid consistency. Disadvantages associated with silica gel include the relatively high cost of silica gel, and the complicated procedure required to prepare a medium using silica gel.

Pectins are routinely used as the thickening or gelling agent in the production of jams and jellies. However, the process generally used involves high sugar concentrations and low pH, neither of which is suitable for general microbial or tissue culture work. In fact, the high sugar and low pH characteristics are useful factors in preventing the establishment of growing, contaminating organisms in the jelly products.

Referring specifically to the prior art, there is disclosed in U.S. Pat. No. 2,970,948, issued to Stevens on Feb. 7, 1961, a culture medium in which pectin may be used. According to the procedure of the Stevens patent, a citrus serum agar culture is prepared by the following steps:

(1) adding pectinesterase to remove pectin by precipitation from fruit juice;
(2) concentrating the fruit juice serum;
(3) mixing with the fruit juice serum certain dry ingredients; and
(4) drying and resulting mixture under a vacuum.

The Stevens patent discloses that included in the dry ingredients must be a gelling agent, which may include agar, gelatin or water soluble salts of pectic acid or alginic acid. It is further indicated that the gelling agent, which may include the pectic acid salts, is to be one which is capable of setting to a gel at room temperature upon cooling an aqueous solution thereof. In contrast to the method and media of the Stevens patent, the present invention involves the combination of a specified type of pectin and cations in the culture media container for biological growth.

In U.S. Pat. No. 2,373,729, issued to Willaman on Apr. 17, 1945, there is disclosed a thickening agent comprising a dry, powdered mixture of pectin, pectase and a water-soluble salt of a polyvalent metal. It is disclosed that the thickening agent is useful in the preparation of jellies, puddings, syrups, catsup, as well as non-food materials. The thickening agent is used by combining the dry-powdered mixture with an aqueous solution under certain conditions of temperature and pH. A different method for making a pectic preparation is disclosed in U.S. Pat. No. 2,540,050, issued to Leo and Taylor on Jan. 30, 1951. A gelatinous pectin/aluminun hydroxide co-precipitate is obtained from a pectin extract of fruit or vegetable material. The co-precipitate is then treated with pectase to provide the pectic material indicated to be useful in preparing jellies. In U.S. Pat. No. 3,360,440, issued to Haab et al., there is disclosed a cold water reconstitutable microbiological medium utilizing a modified cellulose as the sole gelling agent. U.S. Pat. No. 3,935,067, issued to Thayer on Jan. 27, 1976, discloses a culture media comprising inorganic water-swellable support material or water-absorbing clay mineral as a substitute for agar as a growth support and culture media.

A slow-set pectin is disclosed in U.S. Pat. No. 3,835,111, issued to Ehrlich and Cox on Sept. 10, 1974. The pectin material is prepared by contacting pectin with an ammoniacal alcohol solution at low temperature. The resulting pectin has reduced sensitivity to alkaline earth metal ions, which is indicated in the Ehrlich patent as producing a pectin suitable for preparation of sugar jellies. The pectin of the Ehrlich patent has a degree of methylation of 60–70%. A low methoxyl pectin is disclosed in U.S. Pat. No. 3,622,559, issued to Wiles and Smit on Nov. 23, 1971.

In U.S. Pat. No. 3,197,384, issued to Goldman on July 27, 1965, there is disclosed a process for determining the microbial sensitivity to certain anti-microbial agents. In the method of the Goldman patent, the anti-microbial agent is impregnated at premarked areas on a filter pad or sheet of filter paper. The pad or paper is then wetted with an inoculated broth and the reaction of the bacteria in the broth to the anti-microbial agent is perceivable overtime. In contrast to the procedure of the Goldman patent, the present invention relates in one aspect to the impregnation of filter paper or a similar support material with a multivalent metal cation material which will produce gelling of the pectin media when combined therewith.

SUMMARY OF THE INVENTION

The present invention involves the preparation of a gelled biological growth medium in a culture growth container. The method involves the preparation of a liquid growth medium including a low methoxyl pectin which is combined with a suitable amount and type of metal cation within the culture growth container to produce gelling of the medium within the container. In a preferred embodiment, a support material such as a filter pad is impregnated with a metal salt solution and the liquid growth medium is poured over the filter pad in the culture growth container, whereby gelling of the medium subsequently occurs.

It is an object of the present invention to provide a method for preparing a gelled biological growth medium which may be simply and quickly performed.

It is a further object of the present invention to provide a method for preparing a gelled biological growth medium which utilizes relatively inexpensive and readily available materials.

Another object of the present invention is to provide a method for preparing a gelled biological growth medium which does not require the medium to be subjected to elevated temperatures.

A further object of the present invention is to provide a method for preparing a gelled biological growth medium which employs a gelling agent which will not materially interfere with tests using the medium, and which may contribute to the variety of tests which can be used with the growth medium.

It is another object of the present invention to provide a method for preparing a gelled biological growth medium which utilizes materials which may be readily and conveniently packaged in kit form.

It is a further object of the present invention to provide a biological media, and method for producing same, in which pectin is the sole solidifying agent.

Additional objects and advantages of the present invention will become apparent from the description which follows.

DESCRIPTION OF THE PREFERRED EMBODIMENT

Disclosed in the prior art is a variety of culture media and methods for producing the same. The culture media produced in accordance with the teachings of the prior art are well suited generally to the various applications of such media, but certain disadvantages may be associated with these media or methods. The present invention provides a simple and expedient method for preparing a gelled biological growth medium in a culture growth container. Moreover, the method described herein utilizes relatively inexpensive and readily available materials and avoids disadvantages associated with the prior art.

In accordance with the present invention, a liquid culture growth medium is prepared which includes a pectin material. The present invention utilizes a low methoxyl pectin which is defined as having less than about seven percent methoxyl content. Stated in other terms, the low methoxyl pectin has a degree of methoxylation of less than about fifty percent, the degree of methoxylation referring to the esterification with methoxyl groups of the carboxyl groups. In the most preferred embodiment of the present invention the low methoxyl pectin has approximately a five percent methoxyl content, or a degree of methoxylation of from about twenty-five to about forty percent.

The pectin should be present in the growth medium in an amount effective to provide sufficient gelling of the growth medium upon combination of the growth medium with a suitable metal cation material. The amount of pectin will vary with the degree of methoxylation, and also upon other factors such as the extent of gelling desired. However, the amount of pectin desired may be readily determined by simple and direct experimentation. It has been determined that most preferably the pectin, particularly with an approximately five percent degree of methoxylation, is present in an amount of from about ten to about thirty grams of pectin per liter of growth medium.

The liquid growth medium containing the low methoxyl pectin may include a variety of other constituents. In general, the medium may correspond to the wide variety of growth media used in the prior art for microbial and/or tissue cultures, except to the extent that components which would break down or interfere with the pectin should generally not be included. Typically, the culture medium would include several other constituents including 2–10 grams/liter of a carbon source, such as glucose or other sugars, 2–10 grams/liter of nitrogen and other micronutrients in the form of natural products (e.g. tryptone, peptone, beef extract, yeast extract, etc.) or synthetic materials (potassium nitrate and various other microelements). The exact nutrients and concentrations which are useful in the liquid growth medium employed in the present invention are innumerable, and as always in the preparation of a growth medium would be selected according to the particular situation.

The limitations for the other constituents of the medium prepared in accordance with the present invention are generally the same as exist for any other culture media. Typical ranges for certain media components have already been stated. In another aspect, the sugar concentration of the growth medium of the present invention would generally be less than about ten percent, and the pH would preferably range from 3.5 to 8, primarily from about 6 to about 7. In contrast, food products such as jellies or jams would typically include more than fifty percent and perhaps eighty percent sugar as the percent of total solids in the product.

The biological growth medium produced in accordance with the present invention would also preferably include one or more buffers to control the pH of the media. The buffers must be non-toxic to micro-organisms and must not degrade the pectin to a point of uselessness. Generally, buffers containing the element potassium or sodium in combination with phosphate or carbonate groups are non-toxic in minor amounts. Any buffers may cause breakdown or complexing with pectins, and therefore the best results are obtained if the growth medium and the buffers are separately sterilized and then combined after cooling. The variety of buffers which would be useful with the pectin-containing medium include the following: $NaH_2PO_4$, $Na_2HPO_4$, $Na_3PO_4$, $NaHCO_3$ and $Na_2CO_3$, with the tribasic sodium phosphate. ($Na_3PO_4$) being found to be particularly suitable. Other useful buffers would include citric acid and sodium citrate; acetic acid and sodium acetate, citric acid and dibasic sodium phosphate, succinic acid and sodium hydroxide; monobasic sodium or potassium phosphate and dibasic sodium or potassium phosphate; and tris-maleate. The suitability of other buffers or buffer systems are readily predictable and/or determinable by direct and simple experimentation.

In accordance with this invention, an acceptable, solid gel is obtained at a pH of as high as about 9. The prior art literature suggests that pectin as a gelling agent requires an acid pH, typically below about 4. It was therefore an unexpected result that a culture media useful at pH as high as 9 could be obtained using pectin as the gelling agent.

The pectin-containing growth medium is combined with a multivalent metal cation material suitable to produce gelling of the growth medium. It is known in the art that low methoxyl pectin is sensitive to the presence of various multivalent cations such as calcium, and will form gels when combined with such cations. As is well known, the various multivalent metal cations may be provided most readily as the metal salts, most preferably those being water soluble. As in the case of the pectin included in the growth medium, a sufficient amount of metal cations must be provided to produce the desired gelling of the growth media.

In general, the relative amounts of pectin and metal cations to produce adequate gelling are known and undestood in the art, and additionally the amounts desired for use in the present invention may be readily determined by direct experimentation. Sufficient amount of cation is required to produce a good, firm gel formation, but not so much that the gel is hard, brittle or tends to syneresis (weeping). The amounts of the pectin-containing growth medium and/or metal cation material are typically and preferably predetermined to provide the proper gelling, particularly in preparing the materials in a kit form. In the preferred embodiment of the present invention, the cation concentration is about 15–30 milligrams of calcium per gram of pectin. Equivalent amounts of other multivalent metal cations could equally be used. In any event, the amount of cation most preferred will depend on the degree of methoxylation and the amount of the pectin.

The present invention contemplates the combination of the growth medium and metal cations by alternative methods. Most preferably, a support material such as a filter pad or net material is saturated with the proper cation concentration to provide the appropriate amount of metal cations to the amount of growth medium with which it will be combined. A suitable culture growth container, such as a test tube or Petri dish is provided, such container being defined as one which is appropriate and used for containing the medium during culture growth. Typically, the culture growth container is one which permits or facilitates observation or evaluation of the culture growth. The support material with the metal cation material impregnated therein is placed in the culture growth container and the liquid growth medium is added thereto. Contact of the medium with the saturated or impregnated support material with result in a diffusion of the cations through the pectin solution and the consequent formation of a gel. As indicated, the concentration of the cations on the support material and/or the amount of the impregnated support material added to the growth container is determined to provide a suitable amount of the metal cations for gelling of the growth medium.

A net or mesh of natural or synthetic material which will absorb the metal cation material may be used as an alternative to the absorbent pad previously described. A net with a uniform mesh size, such as five millimeters, will provide the function of allowing the observer to have measured fields outlined on the Petri dish or other container. A net or mesh also permits the observer to see completely through the solidified medium rather than limiting viewing from one side as would occur with an opaque, absorbent pad or paper. In addition to using a pad or other support material laid flat in, for example, a petri dish, the support material may alternatively be positioned vertically or at a selected angle from horizontal. Thus, in certain procedures it is desirable to utilize a support material such as a strip of filter paper which may be inserted into a test tube and positioned at an angle from horizontal during gelling of the culture medium.

The method employing a support material for the metal cation material provides several advantages. First, the surface of the growth medium is undisturbed by the combination of the metal cation therewith and a superior surface for the inoculation of microbes is thereby produced. Second, production and sterilization of the various components used in the method are seen to be simply and readily accomplished. Third, this method provides for the use of white, black or variously colored or configured backgrounds for the support material, which enhances the ease of seeing or counting the culture growth on or in the given medium. Although such background materials may also be used while adding the metal cation material by other methods, the method presently described provides a simple and expedient method for both combining the metal cation material and for providing the background.

By an alternate procedure the pectin-containing media is added to the culture growth container and a solution containing the multivalent metal cation is sprayed thereover. This procedure, however, is less desirable in that a less smooth surface on the gel is produced. In addition, it is more difficult to sterilize the atomizer and other equipment needed by this procedure, and it is correspondingly more difficult to maintain a sterile medium. In a third procedure, the metal cation material is directly mixed with the pectin-containing medium. Disadvantages associated with this procedure include the need for a slow acting pectin and/or a slow release cation. The temperature of the pectin solution would also probably need to be elevated. Further, as would exist for the materials for the spraying technique, there would be difficulties in packaging and marketing products for such a procedure since the cation solution would have to be separately sterilized and packaged.

The present invention introduces unique concepts and methodology into the area of preparing biological growth media, and specifically incorporates pectin into such media as the sole gelling or solidifying agent. The present invention provides a simple, straightforward method of utilizing pectin as the sole gelling agent. Particularly in the preferred method of the present invention, preparation of a biological growth medium utilizing pectin as the gelling agent is accomplished by the use of presterilized components not requiring the use of special sterilizing equipment such as an autoclave or oven. For example, the liquid growth medium including pectin may be and preferably is presterilized and packaged, and the support material having the metal cation material therein is correspondingly presterilized and packaged. Also the three essential materials (liquid growth medium, support material, and solution of metal cation material) may be sterilized and packaged separately for later combination. The preparation of a gelled growth medium in a culture growth container may therefore be easily accomplished without substantial time and without the use of other equipment. The preferred embodiment is therefore particularly suited for use in teaching laboratories or other environments where equipment is limited and the time and/or expertise of persons preparing a growth medium are also limited.

Additional advantages are also associated with the method of the present invention. In one aspect, the growth medium including the low methoxyl pectin may be dispensed either hot, warm or chilled, with solidification occurring in any case upon combination with the metal cations. Temperature independence is a particularly notable advantage over the classical agar medium in techniques such as dilution plating for population determination or separation of a mixture of various microbial types. In the dilution technique, an aqueous mixture of the microbes is added to the ungelled medium, mixed for homogeneity, and then poured into Petri dishes and allowed to gel. If agar is used as the gelling agent, the medium must be at a temperature of about 45° C. or higher when the microbes are added due to the fact that solidification will occur below that temperature. Such a high temperature will be harmful to many delicate microbes, and may actually kill or inactivate many, or cause undesirable changes such as mutation. This would be expected to result in an inaccurate picture of the original microbial mixture. Such problems are avoided by the present invention since the microbes can be mixed with the pectin containing medium at as cool a temperature as desired.

The usefulness of the biological growth medium produced in accordance with the present invention is evidenced by the lack of temperature dependence previously described, as well as the fact that most micro-organisms are incapable of hydrolyzing the gelled pectin. The medium may also be used with Procaryotic organisms of the kingdom Protista, with Eucaryotic micro-organisms, or in cell or tissue culture techniques. The medium may also be used in demonstrating which microbes produce pectolytic enzymes, since such organisms may effect the hydrolysis of the media. In addition, the media produced by the procedures of the present invention are easily and accurately reproducible such that a continuing series of experiments or a duplication of an experiment can be performed with accuracy.

The procedures utilized in the present invention are very straightforward and well known to those skilled in the art. As a particular example of the method of the present invention, the following procedure is recited in detail. First, the pectin is blended with the nutrient broth solution at an amount of 20-25 grams per liter and in a manner to avoid the formation of insoluble lumps. The nutrient-pectin broth is then buffered with $Na_3PO_4$ to provide a pH in the range of 6-7. The nutrient-pectin broth is then sterilized in an autoclave at 10-15 pounds per 10-15 minutes. Alternatively the nutrient-pectin broth and the buffers may be sterilized separately and combined following sterilization.

Sterile absorbent pads having approximately the same diameter as the interior of a Petri dish are then placed on the bottom of sterile Petri dishes using sterile forceps. The absorbent pads may be of a variety of configurations as previously indicated, and are then saturated with a predetermined amount of a sterile solution of calcium chloride. Alternatively, other compounds including multivalent metal cations may be employed as is well known in the art relating to agents for use with pectin to provide a gel. Typically, the calcium compounds including chloride, nitrate or phosphate are particularly desirable, and the ideal agent would be water soluble. The calcium chloride solution is then applied to the pad uniformly over its surface with the amount of liquid applied being predetermined to correlate the cation concentration with the amount of pectin present in the nutrient-pectin broth to be added to the Petri dish.

The sterile nutrient-pectin solution is then added over the saturated pad in the Petri dish, utilizing approximately twenty milliliters of the nutrient-pectin broth for a 90 mm dish. Solidification of the medium occurs within 2-3 hours. The solidified medium is then inoculated with micro-organisms, and is incubated either right side up or upside down. Alternatively, the absorbent pads or other support material are saturated with the solidifying agent, i.e. calcium chloride or similar material, prior to sterilization.

The following examples further exemplify biological media prepared in accordance with the present invention.

EXAMPLE I

A general microbiological medium for the growth of bacteria, molds and yeast was formulated as follows.

| | |
|---|---|
| Tryptone | 2 gm |
| Peptone | 2 gm |
| Yeast extract | 2 gm |
| Glucose | 2 gm |
| LM Pectin | 25 gm |
| Deionized water | 1 liter |

This formulation is sterilized by autoclaving and following the autoclaving and cooling of the medium, a combination of $Na_3PO_4$ and $Na_2CO_3$ (presterilized) is added to adjust the pH of the medium.

Numerous bacteria, yeast, and molds have been grown successfully on this formulation.

EXAMPLE II

A specific differential medium known as Eosin Methylene blue agar is used to identify the presence of *Escherichia coli* from other similar bacteria. *E. coli* grows with a green sheen on this medium in comparison to *Enterobacter aerogenes* which grows as a gummy pink culture.

The following medium was prepared which, in preliminary tests, worked very well in differentiating these 2 organisms.

| | |
|---|---|
| Peptone | 5 gm |
| Lactose | 5 gm |
| Eosin y | 0.4 gm |
| Methylene blue | 0.065 gm |
| LM Pectin | 25 gm |
| Deionized water | 1 liter |

The above formulation was sterilized and then adjusted to a pH of 7.1 with $Na_3PO_4$ and $Na_2CO_3$ (presteril).

What is claimed is:

1. A method for preparing a gelled biological growth medium having a pH from about 4 to about 9 in a culture growth container which comprises the steps of:
   a. providing a culture growth container,
   b. preparing a liquid growth medium including between about ten and about thirty grams per liter of growth medium of a low methoxyl pectin material having less than about seven percent methoxyl content to gel the growth medium as the sole gelling agent;

c. introducing a predetermined amount of calcium ions into an absorbent support material and placing the absorbent support material into the culture growth container; and d. combining the growth medium and the calcium ions in said culture growth container to produce gelling of the growth medium.

2. The method of claim 1 in which the low methoxyl pectin material has approximately a five percent methoxyl content.

3. A method for preparing a gelled biological growth medium in a culture growth container which comprises the steps of:

a. providing a culture growth container, said container including therein an absorbent support material containing calcium ions;

b. providing a liquid growth medium having a pH from about 4 to about 9 including between about ten and about thirty grams per liter of growth medium of a low methoxyl pectin material having less than about seven percent methoxyl content as the sole gelling agent for gelling the growth medium; and c. adding the growth medium to the culture growth container in an amount to provide gelling of the growth medium upon contact of the calcium ions with the pectin.

4. The method of claim 3 in which the liquid growth medium includes a buffer selected from the group consisting of $Na_2HPO_4$, $NaH_2PO_4$, $Na_3PO_4$, $NaHCO_3$ and $Na_2CO_3$.

5. The method of claim 3 in which the calcium cations and liquid growth medium including pectin are combined in an amount of between about 15 and about 30 milligrams of calcium cations per gram of pectin.

6. The method of claim 3 in which the low methoxyl pectin material has approximately a five percent methoxyl content.

7. The method of claim 6 in which the calcium cations and liquid growth medium including pectin are combined in an amount of between about 15 and about 30 milligrams of calcium cations per gram of pectin.

* * * * *